US006753009B2

(12) United States Patent
Luber et al.

(10) Patent No.: US 6,753,009 B2
(45) Date of Patent: Jun. 22, 2004

(54) SOFT TABLET CONTAINING HIGH MOLECULAR WEIGHT POLYETHYLENE OXIDE

(75) Inventors: Joseph Luber, Quakertown, PA (US); Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 112 days.

(21) Appl. No.: 10/097,000

(22) Filed: Mar. 13, 2002

(65) Prior Publication Data

US 2003/0175336 A1 Sep. 18, 2003

(51) Int. Cl.$^7$ .................................................. A61K 9/20
(52) U.S. Cl. ........................ 424/441; 424/464; 424/465
(58) Field of Search ................................ 424/435, 441, 424/465

(56) References Cited

U.S. PATENT DOCUMENTS

| 4,818,539 A | | 4/1989 | Shaw et al. |
|---|---|---|---|
| 4,851,226 A | | 7/1989 | Julian et al. |
| 4,882,154 A | | 11/1989 | Yang et al. |
| 4,906,478 A | | 3/1990 | Valentine et al. |
| 5,075,114 A | | 12/1991 | Roche |
| 5,169,645 A | | 12/1992 | Shukla et al. |
| 5,273,758 A | * | 12/1993 | Royce .......................... 424/465 |
| 5,275,822 A | | 1/1994 | Valentine et al. |
| 5,455,049 A | | 10/1995 | Anaebonam et al. |
| 5,489,436 A | | 2/1996 | Hoy et al. |
| 5,626,879 A | | 5/1997 | Anaebonam et al. |
| 5,698,224 A | | 12/1997 | Guittard et al. |
| 6,048,547 A | | 4/2000 | Seth et al. |
| 6,077,538 A | | 6/2000 | Merrill et al. |
| 6,103,260 A | | 8/2000 | Luber et al. |
| 6,149,938 A | * | 11/2000 | Bonadeo et al. ............ 424/464 |
| 6,207,682 B1 | | 3/2001 | Andersen et al. |
| 6,210,699 B1 | | 4/2001 | Acharya et al. |
| 2001/0005728 A1 | | 6/2001 | Guittard et al. |

FOREIGN PATENT DOCUMENTS

| WO | WO 88/06893 A1 | 9/1988 |
|---|---|---|
| WO | WO 99/30717 A1 | 6/1999 |
| WO | WO 00/30617 A1 | 6/2000 |

OTHER PUBLICATIONS

USP23 (Version 1995) <1216> on p. 1981.
USP24 (Version 2000) p. 19–20 and 856.
Lachman, "The Theory & Practice of Industrial Pharmacy", Ch. 11, pp. 293–245, ($3^{rd}$ ed. 1986).
Lieberman, "Pharmaceutical Dosage Forms—Tablets", vol. 2, $2^{nd}$ Ed. 213–217 and 327–329 (1990).

* cited by examiner

Primary Examiner—James M. Spear
(74) Attorney, Agent, or Firm—Michele G. Mangini

(57) ABSTRACT

The invention relates to an immediate release tablet capable of being chewed or disintegrated in the oral cavity, which comprises a pharmaceutically active ingredient, and a matrix comprising polyethylene oxide having a weight average molecular weight of from about 500,000 to about 10,000,000. The tablet possesses exceptionally good mouthfeel and stability.

13 Claims, No Drawings

SOFT TABLET CONTAINING HIGH MOLECULAR WEIGHT POLYETHYLENE OXIDE

The present invention relates to an immediate release, chewable or disintegrable tablet comprising a blend of active ingredient and high molecular weight polyethylene oxide, having exceptionally good mouthfeel and stability.

BACKGROUND OF THE INVENTION

Pharmaceuticals intended for oral administration are typically provided in solid dosage forms such as, for example, tablets, capsules, pills, lozenges, or granules. Tablets are swallowed whole, chewed in the mouth, or dissolved in the oral cavity. Chewable or disintegrable tablets are often employed in the administration of pharmaceuticals where it is impractical to provide a tablet for swallowing whole, for instance with pediatric patients.

Workers in the field continue to try to improve the flavor and mouthfeel of chewable tablets and other comestibles by adding agents, such as gums, thereto. See, e.g., U.S. Pat. No. 4,818,539 and WO 88/06893. In order to effectively texture mask such dosage forms, it is necessary to blend a high level of gum with the active agent. Disadvantageously, during mastication such forms become pasty and initially cause a significant drying phase in the mouth.

Alternative texture masking agents include polyalkylene glycols. For instance, U.S. Pat. No. 4,882,154 discloses chewable dosage forms wherein the pharmaceutical ingredient is pre-coated with, for example, a polyalkylene glycol having a molecular weight of less than 3700. WO 00/30617 discloses a taste masked drug particle having an active inner core, a polyethylene oxide layer covering the core, and an outer taste masking layer. However, these texture masking processes disadvantageously require one or more coating steps, which not only makes them less economical but also increases production cycle time.

Various sustained release dosage forms incorporating polyethylene oxide are also known in the art. See, e.g., U.S. Pat. Nos. 6,207,682, and 6,077,538. However, these dosage forms, which tend to use a substantial amount of polyethylene oxide, are not suitable for applications in which an immediate release of pharmaceutical agent is desired.

It would be desirable to have a chewable or disintegrable, texture masked, immediate release dosage form that could be produced without additional coating process steps.

SUMMARY OF THE INVENTION

This invention relates to an immediate release dosage form capable of being chewed or disintegrated in the oral cavity prior to swallowing, comprising, consisting of, and/or consisting essentially of a. a pharmaceutically active ingredient; and
b. a matrix comprising, based upon the total weight of the dosage form, from about 0.25 percent to about 5 percent of polyethylene oxide having a weight average molecular weight of from about 500,000 to about 10,000,000.

This invention further relates to an immediate release dosage form capable of being chewed or disintegrated in the oral cavity prior to swallowing, comprising, consisting of, and/or consisting essentially of a. a pharmaceutically active ingredient;
b. a matrix comprising, based upon the total weight of the dosage form, from about 0.25 percent to about 5.0 percent of polyethylene oxide having a weight average molecular weight of from about 500,000 to about 10,000,000; and
c. an antioxidant.

DETAILED DESCRIPTION OF THE INVENTION

As used herein, the term "immediate release" shall mean that the dissolution of the dosage form conforms to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19–20 and 856 (1999). The term, "good mouth feel" shall mean that the dosage form becomes a slippery, gel-like mass capable of suspending gritty particles during mastication. By "high weight average molecular weight" it is meant a weight average molecular weight between about 500,000 to about 10,000,000, e.g. from about 1,000,000 to about 7,000,000.

The dosage form of the present invention is made from a composition comprising one or more active ingredients and, based upon the total weight of the dosage form, from about 0.25 percent to about 5 percent, e.g. from about 0.25 percent to about 2.0 percent, of a polyethylene oxide having a high weight average molecular weight.

Suitable active ingredients include pharmaceuticals, minerals, vitamins, other nutraceuticals, and mixtures thereof. Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep aids, urinary tract agents and mixtures thereof.

Examples of suitable gastrointestinal agents include stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine; proton pump inhibitors; gastrointestinal cytoprotectives, such as sucraflate and misoprostol; gastrointestinal prokinetics, such as Prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment, the active agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active agent may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment, the active agent may be selected from pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient(s) are present in the dosage form in a therapeutically effective amount, which is an amount that produces the desired therapeutic response upon oral administration and can be readily determined by one skilled in the art. In determining such amounts, it is well known in the art that various factors must be considered that include, but are not limited to the particular active ingredient being administered, the bioavailability characteristics of the active ingredient, the dose regime, and the age and weight of the patient.

The active ingredient can be in the form of a fine powder, granule, or large crystal, and typically has an average particle size from about 20 microns to about 1000 microns, e.g., from about 50 microns to about 700 microns or from about 100 microns to about 500 microns.

If the active ingredient has an objectionable taste, it may be coated with a known taste masking coating. In one embodiment, the tastemasking coating is substantially free of PEO. As used herein, "substantially free of PEO" shall mean that the tastemasking coating contains, based upon the total weight of the tastemasking coating, less than about 2%, e.g. less than about 1% or less than about 0.1% of PEO. Examples of suitable taste masking coatings are described in U.S. Pat. Nos. 4,851,226, 5,075,114, and 5,489,436, which are all incorporated by reference herein. Other commercially available taste masked active ingredients may also be employed. For example, acetaminophen particles which are encapsulated with ethylcellulose or other polymers by a coaccervation process may be used in the present invention. Such coaccervation-encapsulated acetaminophen may be purchased commercially from Eurand America, Inc. Vandalia, Ohio, or from Circa Inc., Dayton, Ohio.

According to the dosage form of the present invention, the active ingredient is combined with a matrix comprising a high molecular weight polyethylene oxide ("PEO"). In one embodiment, the polyethylene oxide is present in the matrix in the form of a fine powder. That is, the polyethylene oxide has an average particle size of about 1 micron to about 500 microns, e.g., from about 1 micron to about 300 microns or from about 20 microns to about 100 microns, or from about 100 microns to about 250 microns. Without wishing to be bound by theory, it is our belief that the use of such high molecular weight polyethylene oxides having such average particle sizes significantly contributes to the texture masking properties of the final dosage form. This benefit is due, in part, to the fact that such polyethylene oxides may be rapidly hydrated during mastication, which thereby creates a smooth and creamy mouthfeel according to the present invention.

The amount of polyethylene oxide to be used in a dosage form depends on several factors, which include but are not limited to: type and amount of active ingredient, size of dosage form, desired mouthfeel effect, and molecular weight of the polyethylene oxide. Within the ranges of the invention, relatively lower levels of PEO within the upper range of the "high weight average molecular weight" polyethylene oxides and relatively higher levels of PEO within the lower range of the "high weight average molecular weight" polyethylene oxide impart similar mouthfeel function. However, for example, minimal amounts of polyethylene oxide, i.e. less than about 0.25 weight percent, tend to produce an unacceptable, gritty mouthfeel. Further, for example, excessive amounts of polyethylene oxide, i.e. greater than 5 weight percent, tend to produce an unacceptable mouthfeel, which is characterized as initially being overly drying, then as pasty, slimy, and overly viscous.

For optimal dissolution results, it is preferable to employ polyethylene oxides that have average molecular weights in the lower end of the range of "high weight average molecular weight" PEOs as defined herein, and to employ the lowest level of PEOs that yields the desired mouthfeel for the selected active ingredient.

In embodiments wherein a dosage form having a long shelf life is desired, an antioxidant may be included in the matrix in the ratio of antioxidant to polyethylene oxide of from 1:10 to 10:1, e.g. from about 1:10 to about 5:1. That is, the dosage form may comprise an antioxidant in an amount, based upon the total weight of the polyethylene oxide, from about 10 percent to about 1000 percent. Examples of suitable antioxidants include, but are not limited to alpha-tocopherol and derivatives thereof such as tocopherol acetate; butyl hydroxytoluene; butyl hydroxyacetate; tetrabutylhydroxyquinone; propyl gallate; and combinations thereof.

Oil-soluble antioxidants such as those listed here are preferred over water soluble antioxidants such as ascorbic, citric, or fumaric acids, because the oil-soluble group were unexpectedly found to be more effective at preserving the functional properties of the polyethylene oxide, compared with the water-soluble group, which did not retard degradation.

The matrix may optionally contain other conventional auxiliary ingredients, such as fillers, conventional dry binders, sweeteners, disintegrants, and lubricants such as, for example, stearic acid, magnesium stearate, and mixtures thereof. The mixture may also incorporate pharmaceutically acceptable adjuvants, including, for example, preservatives, flavors such as, for example, orange and/or vanilla, acidulants, glidants, surfactants, and coloring agents such as, for example, FD&C yellow. However, the matrix preferably comprises no more than about 25 weight % of such optional auxiliary ingredients.

The dosage form may be made in any manner, and for tablet dosage forms, a variety of tableting methods are known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., *The Theory and Practice of Industrial Pharmacy*, Chapter 11, ($3^{rd}$ Ed. 1986), which is incorporated by reference herein.

In the direct compression tableting method, a blend of the active ingredient, polyethylene oxide, and any other appropriate optional ingredients are directly compacted. In one embodiment employing an antioxidant, the polyethylene oxide and antioxidant may be pre-mixed together prior to blending into the remainder of the ingredients. After all ingredients are blended together, a pre-determined volume of particles from the blend is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar. Advantageously, the direct compression method minimizes or eliminates the use of water-soluble, non-saccharide polymeric binders such as polyvinyl pyrrolidone, alginates, hydroxypropyl cellulose, hydroxypropylmethylcellulose, hydroxyethylcellulose, and the like, which can adversely effect dissolution.

In one embodiment, the tableting method is carried out such that the resulting tablet is relatively soft. The hardness of a "soft" tablet produced in accordance with the present invention is up to about 15 kiloponds per square centimeter (kp/cm$^2$), i.e., e.g., from about 1 kp/cm$^2$ to 8 kp/cm$^2$ or from about 2 kp/cm$^2$ to 6 kp/cm$^2$. Hardness is a term used in the art to describe the diametrical breaking strength as measured by conventional pharmaceutical hardness testing equipment, such as a Schleuniger Hardness Tester. In order to compare values across differently-sized tablets, the breaking strength is normalized for the area of the break (which may be approximated as tablet diameter times thickness). This normalized value, expressed in kp/cm$^2$, is sometimes referred in the art as "tablet tensile strength". A general discussion of tablet hardness testing is found in Leiberman et al., *Pharmaceutical Dosage Forms—Tablets*, Volume 2, 2$^{nd}$ ed., Marcel Dekker Inc., 1990, pp. 213–217, 327–329, which is incorporated by reference herein.

The tablet of the present invention advantageously has acceptable friability. Friability levels are typically less than about 2%, e.g. less than about 1%, or less than about 0.5%. A discussion of tablet friability is presented in USP 23 (1995) <1216> p. 1981.

We have unexpectedly found that the addition of high molecular weight polyethylene oxide to the tablet matrix results in a dosage form that delivers a good mouthfeel through a rapid viscosity build without an initial intense drying sensation of the mouth and without a subsequent excessive slimy or gummy feel during mastication. Although the increase in viscosity will depend upon several factors such as, for example, the amount and molecular weight of polyethylene oxide used and the amount and type of active agent, generally the use of about 0.25 percent to about 5.0 percent of a 500,000 to about 10,000,000 MW polyethylene oxide, based upon the total weight of the dosage form, will result in a viscosity increase during tablet mastication that is similar to that obtained using gums, but without the drying sensation and without the subsequent excessive slimy or gummy feel imparted by using conventional agents.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Production of PEO Tablet and Mouthfeel Evaluation Thereof

A batch of tablets having the formulation set forth in Table A below was made and taste tested for mouthfeel and texture during mastication.

TABLE A

| Ingredient | Tradename | Supplier | Mg/tablet | Theory g/batch |
| --- | --- | --- | --- | --- |
| Polyethylene oxide (5,000,000 MW) | Polyox | Union Carbide | 5 | 0.89 |
| Vitamin E Granulation | 750 SF | BASF | 13.3 | 2.38 |
| Erythritol | | | 100 | 17.88 |
| Crospovidone-NF | | | 25 | 4.47 |
| colorant | | | 2.5 | 0.45 |
| 70.9% Coated Ibuprofen* | | | 282.1 | 50.45 |
| flavorant | | | 15 | 2.68 |
| Sucralose | | | 10 | 1.79 |
| Dextrose monohydrate | | | 658 | 117.67 |
| lubricant | | | 7.5 | 1.34 |
| TOTAL | | | 1118.4 | 200 g |

*Ibuprofen particle coated with Cellulose acetate/Hydroxypropyl Methylcellulose Phthalate/Tween 80 as prepared in accordance with EP 1166777 A1, which is incorporated by reference herein.

After pre-blending the polyethylene oxide with the Vitamin E granulation, the remaining components were added thereto and dry blended until the final mixture was homogeneous. The blend was then compressed using %16" diameter deep concave tooling to a thickness of 0.308" inches and a hardness of 5.2 kp and having a friability of 0.11% after 100 drops.

This procedure was repeated, but with the omission of the polyethylene oxide ingredient.

Samples of the resulting tablets were evaluated by a panel of 13 people in a blinded study for grittiness during mastication. The results of the evaluation demonstrated that the polyethylene oxide-containing tablets had significantly less of a grittiness feel in the mouth in comparison to those tablets lacking the polyethylene oxide.

Example 2

Production of PEO Tablet with Antioxidant for Determination of PEO Stability

A batch of tablets having the formulation set forth in Table B below were made and taste tested for mouthfeel and texture during mastication.

TABLE B

| Ingredient | Tradename | Supplier | Mg/tablet | Theory g/batch |
| --- | --- | --- | --- | --- |
| Polyethylene oxide (7,000,000 MW) | Polyox | Union Carbide | 5 | 1.10 |
| Butyl hydroxytoluene | Tenox | Eastman | 1 | 0.22 |
| Erythritol | | | 150 | 33.11 |
| Crospovidone-NF | | | 22 | 4.86 |
| colorant | | | 2 | 0.44 |
| 74.6% Coated Ibuprofen* | | | 268.1 | 59.18 |
| flavorant | | | 17 | 3.75 |
| Sucralose | | | 10 | 2.21 |
| Dextrose monohydrate | | | 650 | 143.48 |
| lubricant | | | 7.5 | 1.66 |
| TOTAL | | | 1132.6 | 250 g |

*from Example 1

After pre-blending the polyethylene oxide with the butylhydroxytoluene in a plastic bag, the remaining components were added thereto and dry blended until the final mixture was homogeneous. The blend was then compressed using 9/16" diameter deep concave tooling to a thickness of 0.312 inches and a hardness of 4.85 kp and a friability of 0.21%

Samples of the resulting tablets, which were stored in a closed bottle for 12 weeks at 40° C./75% relative humidity, were evaluated for mouthfeel and texture during mastication. The results of the evaluation reflected that the tablets that contained polyethylene oxide and antioxidant had a good meltdown in the mouth and were very creamy when chewed. Samples without the antioxidant were judged gritty after similar storage.

This Example showed that the incorporation of the antioxidant into the composition of the present invention contributes to improving the shelf life of the composition with respect to mouthfeel.

Example 3
Production of PEO Containing Tablets for Determination of Dissolution and Stability A batch of tablets having the formulation set forth in Table C below were made:

TABLE C

| Ingredient | Tradename | Supplier | Mg/tablet | Theory g/batch |
| --- | --- | --- | --- | --- |
| Polyethylene oxide (5,000,000 MW) | Polyox | Union Carbide | 5 | 18.18 |
| Vitamin E Granulation | 750 SF | BASF | 13.3 | 48.36 |
| Erythritol | | | 140 | 509.10 |
| Crospovidone-NF | | | 25 | 90.91 |
| colorant | | | 2.5 | 9.09 |
| 709% Coated Ibuprofen* | | | 282.1 | 1025.82 |
| flavorant | | | 15 | 54.54 |
| Sucralose | | | 10 | 36.36 |
| Dextrose monohydrate | | | 599.6 | 2180.36 |
| lubricant | | | 7.5 | 27.27 |
| TOTAL | | | 1100 | 4000 g |

*from Example 1

After pre-blending the polyethylene oxide with the Vitamin E granulation, the remaining components were added thereto and dry blended until the final mixture was homogeneous. The blend was then compressed using 9/16" diameter deep concave tooling to a thickness of 0.302 inches and a hardness of 4.8 kp and having a friability of 0.08% after 100 drops.

Ibuprofen dissolution at pH 7.2 and 50 rpm is shown in the following table D:

TABLE D

Dissolution of Ibuprofen

| Stability Condition | Container | 15 min | 30 min | 45 min |
| --- | --- | --- | --- | --- |
| Initial | Bulk | 90.63 | 98.90 | 101.03 |
| 1 wk 30/70 | open | 91.87 | 97.23 | 98.80 |
| 1 wk 50C | Closed HDPE | 94.97 | 98.17 | 98.93 |
| 4 wk 40/75 | Closed HDPE | 95.33 | 98.47 | 98.83 |
| 8 wk 40/75 | Closed HDPE | 95.47 | 97.77 | 100.47 |
| 12 wk 40/75 | Closed HDPE | 94.87 | 98.27 | 98.97 |
| 26 wk 40/75 | Closed HDPE | 92.93 | 95.87 | 96.73 |

This Example showed that the compositions of the present invention retained their immediate release properties for an extended shelf life period.

We claim:

1. An immediate release dosage form capable of being chewed or disintegrated in the oral cavity prior to swallowing, comprising:

a. a pharmaceutically active ingredient; and b. a matrix comprising, based upon the total weight of the dosage form, from about 0.25 percent to about 5 percent of polyethylene oxide having a weight average molecular weight of from about 500,000 to about 10,000,000, wherein the active ingredient is selected from the group consisting of bisacodyl, famotadine, ranitidine, cimetidine, prucalopride, diphenoxylate, loperamide, lactase, mesalamine, bismuth, antacids, and pharmaceutically acceptable salts, esters, isomers, and mixtures therof.

2. An immediate release dosage form capable of being chewed or disintegrated in the oral cavity prior to swallowing, comprising:
   a. a pharmaceutically active ingredient; and
   b. a matrix comprising, based upon the total weight of the dosage form, from about 0.25 percent to about 5 percent of polyethylene oxide having a weight average molecular weight of from about 500,000 to about 10,000,000,
wherein the active ingredient is selected from the group consisting of acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

3. An immediate release dosage form capable of being chewed or disintegrated in the oral cavity prior to swallowing, comprising:
   a. a pharmaceutically active ingredient; and
   b. a matrix comprising, based upon the total weight of the dosage form, from about 0.25 percent to about 5 percent of polyethylene oxide having a weight average molecular weight of from about 500,000 to about 10,000,000,
wherein the active ingredient is selected from the group consisting of pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

4. An immediate release dosage form capable of being chewed or disintegrated in the oral cavity prior to swallowing, comprising:
   a. a pharmaceutically active ingredient; and
   b. a matrix comprising polyethylene oxide having a weight average molecular weight of from about 500,000 to about 10,000,000, wherein the dosage form contains, based upon the total weight of the dosage form, from about 0.25 percent to about 2.0 percent of polyethylene oxide.

5. An immediate release dosage form capable of being chewed or disintegrated in the oral cavity prior to swallowing, comprising:
   a. a pharmaceutically active ingredient;
   b. a matrix comprising, based upon the total weight of the dosage form, from about 0.25 percent to about 5.0 percent of polyethylene oxide having a weight average molecular weight of from about 500,000 to about 10,000,000; and
   c. an antioxidant.

6. The dosage form of claim 5 wherein the antioxidant is selected from the group consisting of alpha-tocopherol and derivatives thereof; butyl hydroxytoluene; butyl hydroxyacetate; tetrabutylhydroxyquinone; propyl gallate; and mixtures thereof.

7. The dosage form of claim 5, wherein the active ingredient is selected from the group consisting of bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

8. The dosage form of claim 5, wherein the active ingredient is selected from the group consisting of acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

9. The dosage form of claim 5, wherein the active ingredient is selected from the group consisting of pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

10. The dosage form of claim 5, wherein the dosage form is a tablet.

11. The dosage form of claim 5, wherein the polyethylene oxide has a weight average molecular weight of from about 2,000,000 to about 5,000,000.

12. The dosage form of claim 5 containing, based upon the weight of the polyethylene oxide, from about 10 percent to about 1000 percent of the antioxidant.

13. The dosage form of claim 5, wherein the pharmaceutically active ingredient is coated with a taste masking coating, wherein said taste masking coating is substantially free of polyethylene oxide.

* * * * *